United States Patent [19]

Sofia

[11] Patent Number: 5,292,772
[45] Date of Patent: Mar. 8, 1994

[54] METHOD FOR THE PREVENTION AND CONTROL OF EPILEPTIC SEIZURE ASSOCIATED WITH LENNOX-GASTAUT SYNDROME

[75] Inventor: Robert D. Sofia, Willingboro, N.J.

[73] Assignee: Carter-Wallace, Inc., New York, N.Y.

[21] Appl. No.: 966,964

[22] Filed: Oct. 26, 1992

Related U.S. Application Data

[63] Continuation-in-part of Ser. No. 626,198, Dec. 7, 1990, abandoned, which is a continuation-in-part of Ser. No. 412,964, Sep. 26, 1989, Pat. No. 4,978,680.

[51] Int. Cl.$^5$ .............................................. A61K 31/24
[52] U.S. Cl. .................................................. 514/534
[58] Field of Search ...................................... 514/534

[56] References Cited

PUBLICATIONS

Chem-Abst. 104-180056v (1986).

Primary Examiner—S. J. Friedman
Attorney, Agent, or Firm—Kevin B. Clarke

[57] ABSTRACT

A novel method for the prevention and control of epileptic seizures, particularly intractable seizures associated with the Lennox-Gastaut syndrome, employing pharmaceutical compositions containing 2-phenyl-1,3-propanediol dicarbamate.

1 Claim, No Drawings

METHOD FOR THE PREVENTION AND CONTROL OF EPILEPTIC SEIZURE ASSOCIATED WITH LENNOX-GASTAUT SYNDROME

This application is a continuation-in-part of Ser. No. 07/626,198, filed Dec. 7, 1990, now abandoned, which is a continuation-in-part of U.S. Pat. No. 412,964, filed Sep. 26, 1989, now U.S. Pat. No. 4,978,680.

The present invention relates to pharmaceutical compositions containing 2-phenyl-1,3-propanediol dicarbamate as an active component and to methods for the prevention and control of epileptic seizures by the use of such compositions.

More particularly, the present invention further relates to methods for increasing epileptic seizure threshold and the prevention of epileptic seizure spread through the administration of therapeutic compositions which contain as an active ingredient 2-phenyl-1,3-propanediol dicarbamate commonly known as Felbamate.

Felbamate is a well known pharmaceutical compound having been described in U.S. Pat. Nos. 2,884,444 and 4,868,327.

Epilepsy, a disease which has been characterized as a paroxysmal, self-sustaining and self-limited cerebral dysrhythmia, genetic or acquired in origin and physiologic or organic in mechanism is generally divided into four main types based on the type of seizure that occurs in those afflicted with the disease.

Based on clinical and electroencephalographic observations, the four general subdivisions of epilepsy are:
1. Grand mal
2. Petit mal
3. Psychomotor
4. Autonomic Those afflicted with epilepsy may present with any one of or a mixture of the foregoing forms of the disease.

In theory, it is believed that anti-epileptic drugs act to prevent or control seizures by acting on the seizure focus which may be a collection of pathologically altered neurons or normal cells having restricted vascular supply or an injured area in which the neurons of a nerve net have been destroyed.

Up to the present time, all drugs used in the treatment of epilepsy function as prophylactics against the symptoms of epilepsy, i.e., the reduction and control of epileptic seizures as opposed to being curatives.

Although it is generally recognized that approximately 50% of epileptic patients can be controlled with presently available anti-epileptic medications, there is a continuing long felt need for more selective and less toxic anti-epileptic drugs. The desiratum of the art has been to provide a non-toxic, non-sedative, long-acting and highly effective anti-epileptic drugs.

Phenytoin and carbamazepine are presently the drugs of choice for control of both generalized tonic-clonic (grand mal) and complex partial (temporal lobe) epileptic seizures.

In addition to gingival hyperplasia and hirsutism peculiar to phenytoin, both drugs have been reported to induce cerebellar-vestibular effects, skin disorders, hepatic deficiencies and congenital abnormalities. The foregoing toxicity profile for both phenytoin and carbamazepine clearly demonstrates a need for less toxic substances for use as anti-epileptic medications.

One of the objects of the present invention is to provide compositions for the treatment of epilepsy comprising felbamate as the active ingredient.

Another object of the present invention is to provide relatively non-toxic compositions effective to control or prevent epileptic seizures which have a unique spectrum of anti-epileptic activity and which include felbamate as an active component.

A further object of the present invention is to provide compositions for the prevention and control of epileptic seizures which compositions are relatively non-toxic, have a high degree of effectiveness and continue to produce a therapeutic response over relatively long periods of time.

Still another object of the present invention is to provide a method for the prevention and control of seizures associated with Lennox-Gastaut syndrome.

Moreover, it is an object of the present invention to provide methods for the prevention and control of epileptic seizures through the use of felbamate.

Accordingly, it has been found that felbamate chemically described as 2-phenyl-1,3-propanediol dicarbamate is a compound which has demonstrated superior properties when compared to prototype drugs, i.e., phenytoin with respect to increasing seizure threshold and prevention seizure spread.

The compositions for the treatment of epilepsy may take any of a variety of forms although they are intended primarily for oral use and is suitable for forming into pills, capsules and tablets by well-known practices. When the active ingredient is in the form of a solid, a typical tablet composition comprises 500 milligrams of 2-phenyl-1,3-propanediol dicarbamate intermixed in a dry pulverulent state with suitable solid carriers and diluents.

In general, an effective daily dose of the active ingredient is in the range of from about 100 milligrams to about 5 grams.

Solid carriers and diluents suitable for use include sugars such as lactose and sucrose; cellulose derivatives such as carboxymethyl cellulose, ethyl cellulose, methyl cellulose, etc., gelatin including hard and soft gelatin capsules, talc, cornstarch, stearic acid and magnesium stearate.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets. However, for convenience in manufacturing and ease of administration, it is preferable that each dosage form contains at least 25 milligrams and up to 500 milligrams of 2-phenyl-1,3-propanediol dicarbamate per unit dosage form.

EXAMPLE 1

2-phenyl-1,3-propanediol dicarbamate is constituted into 500 mg. dosage units by encapsulation without an adjuvant into hard gelatin capsules. The yield from 1000 g. of 2-phenyl-1,3-propanediol dicarbamate is about 2000 capsules each containing 500 mg. of medicant.

EXAMPLE 2

A tableting formulation is prepared as follows:
83 g. 2-phenyl-1,3-propanediol dicarbamate
13 g. powdered sugar with 3% starch
76 g. corn syrup q.s. water
13 g. talc U.S.P. powdered Italian
3 g. magnesium stearate
q.s. alcohol
flavoring The formulation is compressed into tablets, each containing 200 mg. of 2-phenyl-1,3-propanediol dicarbamate. The yield is about 1750 tablets.

Felbamate (2-phenyl-1,3-propanediol dicarbamate) has a very favorable preclinical profile characterized by a substantial margin of safety (protective index 16.9–19.1). The following example presents the results from a double-blind randomized clinical trial in patients with partial seizures. Criteria for patient entry into the study were 4 or more complex partial seizures per month in spite of treatment with both phenytoin and carbamazepine.

EXAMPLE 3

Fifty-six patients (mean age 31.4 years; male=32, female=24) completed the study. The mean seizure frequencies for the eight week periods analyzed were: baseline=39.8; felbamate=34.9; placebo=40.2. Felbamate was significantly superior to placebo by percent seizure reduction (p=0.018) and truncated percent seizure reduction (p=0.007).

The mean felbamate dose was 2300 mg/day. Plasma felbamate concentrations ranged from 18.4 to 51.9, mean=32.5 mg/ml.

Adverse effects were minor and consisted of nausea and CNS effects.

The superiority of felbamate over placebo in a population of persons with severely refractory epilepsy indicates this medication to be a major anti-epileptic agent.

The Lennox-Gastaut syndrome is characterized by mental retardation, slow spike-and-wave EEG and intractable seizures. Example 4, which follows, demonstrates the effectiveness of Felbamate in the treatment of Lennox-Gastaut syndrome.

EXAMPLE 4

Six patients ranging in age from 6–30 years (average 14.5 years) were treated with Felbamate. All of the patients had completed a double-blind study, were on two standard antiepileptics and were having a minimum of 90 seizures/month. Treatment length ranged from 1–4 months. Felbamate dose ranged between 45 and 58 mg/kg/day (maximum dose 3600 mg/day). Two of the subjects experienced a 50% reduction of seizures and three of the subjects had a 75–100% reduction of seizures. Two patients experienced at least one or more seizure free weeks.

In conclusion, results suggest that Felbamate is an effective treatment for the seizures associated with the Lennox-Gastaut syndrome.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kinds of concurrent treatment, if any, frequency of treatment and the nature of the effect desired. Usually, a daily dosage of active ingredient compound will be from about 1–500 milligrams per day. Ordinarily, from about 100 to about 500 milligrams per day in one or more applications is effective to obtain desired results.

The active ingredient can be administered orally in solid dosage forms, such as capsules, tablets and powders, or in liquid dosage forms such as elixirs syrups and suspensions. It can also be administered parenterally in sterile liquid dosage forms.

Gelatin capsules contain the active ingredient and powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite or ascorbic acid, either alone or combined, are suitable stabilizing agents. Also used are citric acid and its salts and sodium EDTA. In addition, parenteral solutions can contain preservatives such as benzalkonium chloride, methyl- or propylparaben and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules: A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets: A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Suspension: An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agents. When the drugs are administered in physical combination, the dosage form and administration route should be selected for compatibility with both drugs.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets.

In general, an effective daily dose of the active ingredient is in the range of from about 100 milligrams to about 5 grams.

Felbamate (2-phenyl-1,3-propanediol dicarbamate) has a very favorable preclinical profile characterized by a substantial margin of safety (protective index 16.9–19.1).

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for the prevention and control of seizures associated with Lennox-Gastaut syndrome which comprises administering to a warm-blooded animal in need of such treatment 2-phenyl-1,3-propanediol dicarbamate in a daily dosage of from about 100 milligrams to about 5 grams.

* * * * *